United States Patent [19]

Drewlow

[11] Patent Number: Plant 7,284

[45] Date of Patent: Jul. 31, 1990

[54] KALANCHOE PLANT NAMED BASHFUL

[75] Inventor: Lyndon W. Drewlow, Ashtabula, Ohio

[73] Assignee: Mikkelsens, Inc., Ashtabula, Ohio

[21] Appl. No.: 318,057

[22] Filed: Mar. 2, 1989

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 5,362 12/1984 Finger ..... Plt. 68

P.P. 5,533 8/1985 Mikkelsen ..... Plt. 68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Bashful particularly characterized by its ability to produce cut flowers. Bashful has strong upright branches and stems which carry salmon rose flowers, excellent lateral branching, large flower size, open inflorescence, and long lasting flowers which do not fade and which remain open under low light conditions.

1 Drawing Sheet

The present invention relates to a new and distinctive cultivar of Kalanchoe plant, botanically known as *Kalanchoe blossfeldiana,* and known by the cultivar name Bashful. The new cultivar was developed by me through controlled breeding by crossing Mikkelsen Seedling No. 82-557-2 (seed parent) with Desert Rose (pollen parent). The principal objective of the breeding program was to develop new Kalanchoe cultivars having certain desired characteristics and which could be used to produce cut flowers.

Asexual reproduction of stem cuttings has shown that the unique features of this new Kalanchoe are stabilized and are reproduced true to type in successive propagations.

The following characteristics distinguish the new kalanchoe from both its parent cultivars and other cultivated kalanchoes of this type known and used in the floriculture industry. In order to describe the characteristics more meaningfully, references are made to known pot type kalanchoe cultivars, including Eternity (U.S. Plant Pat. No. 5,253), Seraya (U.S. Plant Pat. No. 5,362), and Citation (U.S. Plant Pat. No. 5,533). Also referred to are Desert Blaze, Sombrero, Lemon Drop and Passionate, all cut flower type cultivars of applicant disclosed in pending plant patent applications.

1. Bashful is upright, tall cut flower type Kalanchoe characterized by distinct salmon rose flowers. Eternity has salmon orange flowers, Seraya has salmon pink flowers, and Citation has pink flowers.

2. Bashful is much taller (48–52 cm) than Eternity, Citation, and Seraya (all 18–22 cm tall), is similar in size to Desert Blaze, is slightly taller than Sombrero and Passionate (both 43–47 cm), but not as tall as Lemon Drop (53–57 cm).

3. Bashful has ten lateral branches similar to Passionate, Sombrero and Eternity, while Citation, Seraya, Desert Blaze, and Lemon Drop usually have eight lateral branches.

4. Flower size of Bashful (22 mm) is larger than any of the comparison cultivars.

5. Leaves of Bashful are the smallest of any of the comparison cultivars, with Eternity, Citation and Passionate having the next smallest leaves.

6. Mature stigmatic surfaces of Bashful have a reddish pink tint as do Passionate, Desert Blaze and Seraya.

Citation, Eternity, Sombrero, and Lemon Drop have only a whitish color.

7. Leaf margins are finely lobed and deeply cut like Passionate, Eternity and Desert Blaze, with the other comparison cultivars having shallower cut and larger lobed margins.

8. Bashful has the darkest green leaf color of the cut flower types, with only Eternity of the pot types having as dark a green leaf.

9. The inflorescence of Bashful and the other four cut flower types are open with flowers carried at the end of long strong branches, while the pot types have a dense compact inflorescence with flowers carried at the end of short branches.

10. The five cut flower type kalanchoes tend to have very little basal branching from the lower two nodes, while the three pot plant types have much more basal branching.

11. Long lasting salmon rose flowers that do not fade once the flower is fully open.

12. Strong, upright branches.

13. Flowers remain open under low light conditions after one dark to light conditioning cycle after cutting.

14. Can be grown on a schedule to provide cut flowers every week of the year.

The accompanying colored photograph is a top perspective view showing the overall appearance of Bashful. The photograph depicts color as true as it is reasonably possible to obtain in a colored reproduction of this type. The photograph was taken in late June, 1988.

The following is a detailed description of my new Kalanchoe cultivar based on plants produced under commercial practices in Ashtabula, Ohio, under greenhouse conditions. Color references are made to The Royal Horticultural Society Colour Chart except where general color terms of ordinary dictionary significance are used.

The description is based on plant cuttings five (5) weeks old stuck in six (6) inch pots and given two (2) weeks of long days and then short days to induce flowering. The plants were grown at 64°–68° F. night temperatures. Measurements were taken twelve (12) weeks after the start of short days, with plant height being measured from the soil line of the plant.

Parentage: A controlled cross between Mikkelsen Seedling No. 82-557-2 as female parent and Desert Rose as male parent.

Propagation:

(A) *Type cutting.*—Stem tip cutting up to 3 cm long.

(B) *Time to root.*—10 days at 21° C. summer; 14 days at 21° C. winter.

(C) *Rooting habit.*—Numerous, fine, fibrous roots.

Plant description:

(A) *Form.*—Tall (48–52 cm), upright, with flower clusters (inflorescence) carried above the main leaf mass on long stems; leaves are small, with the smallest being in the flower cluster.

(B) *Habit of growth.*—Upright, vigorous branching primarily from the middle nodal area of plant to produce a spray form of flower cluster. Environment will play a role in how tall a plant will get.

(C) *Foliage.*—Leaves simple and opposite. (1) Size: Average full grown leaves are 90 to 100 mm long and 50 to 60 mm wide on a plant grown in a 15 cm pot. Growth conditions will cause leaf size to vary. (2) Shape: Ovate to obovate; apex obtuse; base rounded. (3) Texture: Glabrous, coriaceous and succulent. (4) Margin: Crenated. (5) Young foliage, top side 146A; Young foliage, under side 146C; Mature foliage, top side 147A; Mature foliage, under side 147B.

Flowering description:

(A) *Flowering habits.*—Inflorescence is a cyme. Terminal flower on main axis opens first followed by the terminal flowers of the side branches, continuing with the subsequent development of branches in the inflorescence. Inflorescence is made up of the main stem and up to ten lateral branches. The inflorescence is 36–39 cm in height and approximately 14–18 cm in width, and is open.

(B) *Natural flowering season.*—Early January. Flowering time under controlled daylength at 20° C. in summer is nine weeks; in winter is twelve weeks. Flowering time depends to temperature, light intensity and other growing conditions. In general, higher temperatures (to the point of heat delay) and increased light intensity will speed up flowering and low temperatures and light intensity will delay flowering. Other conditions that can cause delay in the flowering are low fertility, very high night temperatures (80° F. plus) and moisture stress.

(C) *Flower buds.*—Oblong, up to 12 mm long before showing first color, developing tublar as flower petals mature. Sheathed with four green sepals.

(D) *Flower borne.*—Compound dichasial cymes, primary peduncle 4 mm in diameter just below the first branch of the inflorescence; length will vary depending on growing conditions. In general peduncles will be shorter when plants are moisture stressed, grown well spaced, grown under high light intensity, grown under low temperatures, or are given applications of growth regulators. If plants are grown crowded and/or under low light conditions, the peduncles will tend to stretch badly. Pedicels will vary in length depending on where located in inflorescence. Indeterminate flowering nature. The pedicels become shorter the higher they are in the inflorescence, that is, the closer they are to the apical meristem.

(E) *Quality of flowers.*—Very floriferous, with more than 100 flowers on the main stem and 50 or more flowers on each of the ten lateral branches.

(F) *Petals.*—(1) Shape: Nearly rounded, top cuspidate. (2) Color: top side when opening between 47B and 47C, fading to 68C; under side, 48B and 49B. (3) Number of Petals: 4. (4) Size: 11 mm long and 7 mm wide; flower diameter 22 mm.

(G) *Reproductive organs.*—(1) Number of Stamens: Eight. (a) Anther shape: Flat elliptical; color — yellowish-green. (b) Filament color: Whitish green. (c) Pollen color: Yellow. (2) Pistils: (a) Stigma shape: Flat; color — white with reddish pink tint. (b) Style color: Yellowish green. (c) Ovaries: Number — 4; size — 8 mm; color — green.

Disease resistance: Bashful has shown resistance to mildew.

I claim:

1. A new and distinct cultivar of Kalanchoe plant named Bashful, as illustrated and described.

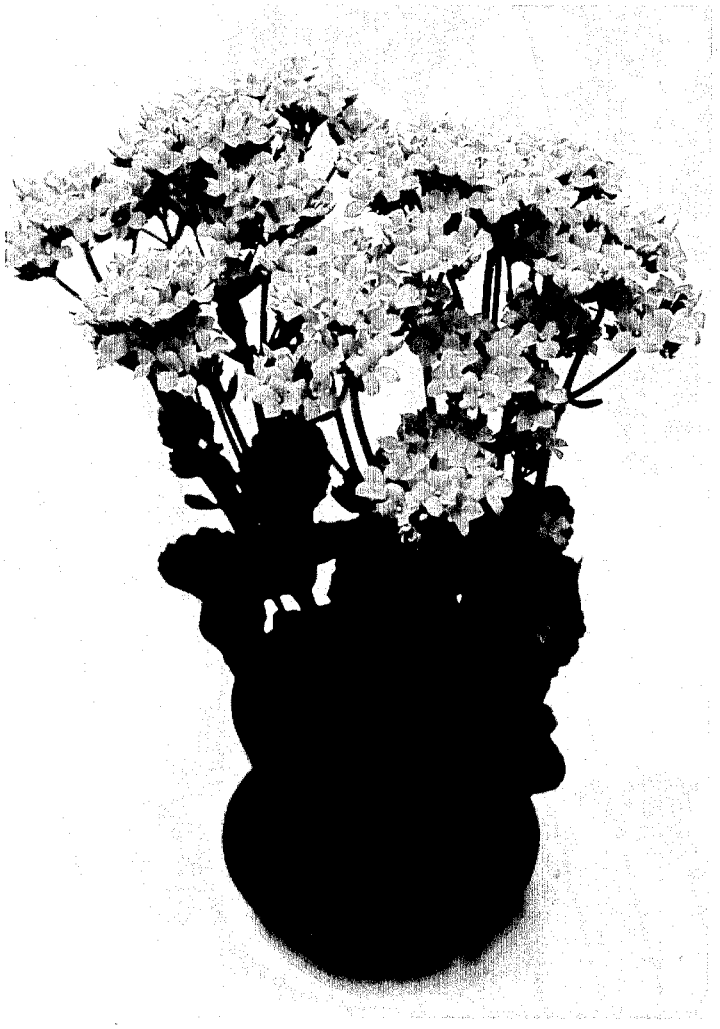

* * * * *